United States Patent
Nagata et al.

(10) Patent No.: US 8,003,675 B2
(45) Date of Patent: Aug. 23, 2011

(54) 3,4-DIHALOGENOISOTHIAZOLE DERIVATIVE, AND AGRICULTURAL OR HORTICULTURAL PLANT DISEASE-CONTROLLING AGENT

(75) Inventors: Toshihiro Nagata, Iwata (JP); Atsushi Kogure, Tokyo (JP); Isao Kaneko, Tokyo (JP); Norihisa Yonekura, Tokyo (JP); Ryo Hanai, Tokyo (JP)

(73) Assignees: Kumiai Chemical Industry Co., Ltd., Tokyo (JP); Ihara Chemical Industry Co., Ltd., Tokyo (JP)

( * ) Notice: Subject to any disclaimer, the term of this patent is extended or adjusted under 35 U.S.C. 154(b) by 71 days.

(21) Appl. No.: 12/227,397

(22) PCT Filed: Jul. 6, 2007

(86) PCT No.: PCT/JP2007/000737
§ 371 (c)(1),
(2), (4) Date: Nov. 17, 2008

(87) PCT Pub. No.: WO2008/007459
PCT Pub. Date: Jan. 17, 2008

(65) Prior Publication Data
US 2009/0240057 A1    Sep. 24, 2009

(30) Foreign Application Priority Data
Jul. 12, 2006 (JP) .................. 2006-191972

(51) Int. Cl.
| | | |
|---|---|---|
| *A61K 31/4025* | (2006.01) | |
| *A61K 31/4155* | (2006.01) | |
| *A61K 31/4178* | (2006.01) | |
| *A61K 31/4192* | (2006.01) | |
| *C07D 275/04* | (2006.01) | |
| *C07D 275/02* | (2006.01) | |
| *C07D 285/06* | (2006.01) | |
| *C07D 271/02* | (2006.01) | |
| *C07D 277/02* | (2006.01) | |

(52) U.S. Cl. ........ 514/361; 514/362; 514/363; 514/364; 514/365; 514/366; 514/367; 514/372; 514/373; 548/203; 548/127; 548/128; 548/131; 548/134; 548/136; 548/143; 548/152; 548/153; 548/202; 548/180; 548/207

(58) Field of Classification Search ................. None
See application file for complete search history.

(56) References Cited

U.S. PATENT DOCUMENTS
5,240,951 A    8/1993 Shimotori et al. ............ 514/372
6,310,005 B1 *  10/2001 Assmann et al. ............. 504/223

FOREIGN PATENT DOCUMENTS
| JP | 2003-146975 | 5/2003 |
| JP | 2005-082486 | 3/2005 |
| WO | WO 95/31448 | 11/1995 |

OTHER PUBLICATIONS
Translated Detailed Description JP 05-059024, published Sep. 3, 1993.*

* cited by examiner

*Primary Examiner* — Yong Chu
*Assistant Examiner* — Michael Barker
(74) *Attorney, Agent, or Firm* — Bacon & Thomas, PLLC

(57) ABSTRACT

A 3,4-dihalogenoisothiazole derivative represented by the general formula [I]

[formula 1]

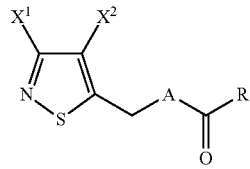

(wherein $R^1$ is a halogen atom; A is an oxygen atom or a sulfur atom; and R is a $C_1$-$C_6$ alkyl group, a $C_2$-$C_5$ alkenyl group, a $C_2$-$C_5$ alkynyl group, a $C_3$-$C_6$ cycloalkyl group, a phenyl group or a 5- to 10-membered heterocyclic group containing at least one of oxygen atom, sulfur atom and nitrogen atom), or a salt thereof.

6 Claims, No Drawings

3,4-DIHALOGENOISOTHIAZOLE DERIVATIVE, AND AGRICULTURAL OR HORTICULTURAL PLANT DISEASE-CONTROLLING AGENT

TECHNICAL FIELD

The present invention relates to a 3,4-dihalogenoisothiazole derivative or a salt thereof, as well as to an agricultural or horticultural plant disease-controlling agent containing the derivative or the salt thereof as an active ingredient.

BACKGROUND ART

It has been known that some isothiazole derivatives have an activity for control of plant diseases (Patent Literature 1). The compounds described in the literature, however, are compounds in which methyl group is bonded to the 3-position of isothiazole ring, and the literature describes no 3,4-dihalogenoisothiazole derivative represented by the general formula [I] of the present application.

Patent Literature 1: JP-A-2005-82486

DISCLOSURE OF THE INVENTION

Task to Be Achieved by the Invention

In cultivation of agricultural or horticultural crops, a large number of disease-controlling agents are in use for diseases of crops. However, with conventional disease-controlling agents, there are cases that the effect of disease control is insufficient or the use of controlling agent is restricted owing to the emergence of pathogenic fungi having chemical resistance; and a considerable number of conventional disease-controlling agents are not satisfactory in that they give chemical injury or stain to plants, or have toxicity to men, beasts and fishes, and give adverse effects on environment. Therefore, it is strongly desired to develop a disease-controlling agent which is low in such drawbacks and can be used safely.

The task of the present invention is to solve the above-mentioned problems of conventional plant disease-controlling agents and further provide a plant disease-controlling agent which is superior in controlling effect, residual activity, etc.

Means for Achieving the Task

In order to achieve the above task, the present inventors synthesized a large number of 3,4-dihalogenoisothiazole derivatives whose plant disease-controlling activities were unknown, and investigated their plant disease-controlling activities and usefulnesses. As a result, it was found that the 3,4-dihalogenoisothiazole derivative or salt thereof of the present invention (hereinafter referred to as the present invention compound), when applied to plants, shows a plant disease-controlling activity over a long period and gives a striking plant disease-controlling effect to plants with no chemical injury thereto. The finding has led to the completion of the present invention.

The present invention relates to any of the following (1) to (4).

(1) A 3,4-dihalogenoisothiazole derivative represented by the general formula [I]

[formula 1]

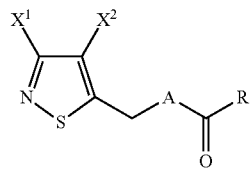

[wherein $X^1$ and $X^2$ are each a halogen atom;

A is an oxygen atom or a sulfur atom; and

R is a $C_1$-$C_6$ alkyl group (the group may be mono- or poly-substituted by halogen atom), a $C_2$-$C_5$ alkenyl group (the group may be mono- or poly-substituted by phenyl group), a $C_2$-$C_5$ alkynyl group, a $C_3$-$C_6$ cycloalkyl group, a phenyl group (the group may be mono- or poly-substituted by same or different substituents selected from the following substituents group α), or a 5- to 10-membered heterocyclic group containing at least one of oxygen atom, sulfur atom and nitrogen atom (the group may be mono- or poly-substituted by same or different substituents selected form the following substituents group α)], or a salt thereof.

[Substituents Group α]

$C_1$-$C_6$ alkyl group, $C_3$-$C_6$ cycloalkyl group, $C_1$-$C_6$ haloalkyl group, phenyl group, halogen atom, cyano group, $C_1$-$C_5$ acyl group, carboxyl group, $C_1$-$C_6$ alkoxycarbonyl group, mono($C_1$-$C_6$ alkyl)carbamoyl group, di($C_1$-$C_6$ alkyl)carbamoyl group, amino group, mono($C_1$-$C_6$ alkyl)amino group, di($C_1$-$C_6$ alkyl)amino group, $C_1$-$C_6$ alkylamide group, $C_1$-$C_6$ alkylsulfonamide group, nitro group, hydroxyl group, $C_1$-$C_6$ alkoxy group, $C_1$-$C_6$ acyloxy group, $C_1$-$C_6$ alkylsulfonyl group, mono($C_1$-$C_6$ alkyl)sulfamoyl group, di($C_1$-$C_6$ alkyl)sulfamoyl group (2) A 3,4-dihalogenoisothiazole derivative or a salt thereof, according to (1), wherein the 5- to 10-membered heterocyclic group containing at least one of oxygen atom, sulfur atom and nitrogen atom is pyridine, pyrrole, furan, thiophene, oxazole, thiazole, imidazole, isoxazole, isothiazole, pyrazole, oxadiazole, thiadiazole, triazole, indole, benzofuran, benzothiophene, benzoxazole, benzothiazole, benzoimidazole, benzoisoxazole, benzoisothiazole, indazole, benzoxadiazole, benzothiadiazole, or benzotriazole.

(3) A 3,4-dihalogenoisothiazole derivative or a salt thereof, according to (1) or (2), wherein R is $C_1$-$C_6$ alkyl group, $C_2$-$C_5$ alkenyl group, phenyl group (the group may be substituted by same or different, 1 to 5 substituents selected from the group consisting of $C_1$-$C_6$ alkyl group, halogen atom, cyano group, $C_1$-$C_6$ alkoxycarbonyl group, nitro group, $C_1$-$C_6$ alkoxy group and $C_1$-$C_6$ alkylsulfonyl group), pyridine (the group may be substituted by same or different, 1 to 4 substituents selected from the group consisting of $C_1$-$C_6$ alkyl group and halogen atom), isothiazole (the group may be substituted by same or different, 1 to 2 substituents selected from the group consisting of $C_1$-$C_6$ alkyl group and halogen atom), or benzothiadiazole (the group may be substituted by same or different, 1 to 3 substituents selected from the group consisting of $C_1$-$C_6$ alkyl group and halogen atom).

(4) An agricultural or horticultural plant disease-controlling agent containing, as an active ingredient, a 3,4-dihalogenoisothiazole derivative or a salt thereof, according to any of (1) to (3).

Effect of the Invention

The 3,4-dihalogenoisothaizole derivative or salt thereof, of the present invention is a novel compound. Also, the agricultural or horticultural plant disease-controlling agent of the present invention is characterized by giving no chemical injury to crops and showing high controlling effects to rice blast disease, cucumber anthracnose, etc.; therefore, it is useful as an agricultural or horticultural plant disease-controlling agent.

BEST MODE FOR CARRYING OUT THE INVENTION

The definitions of the symbols and terms used in the present Description are given below.

In the formula [I], the substituents $X^1$ and $X^2$ indicate each a halogen atom. The halogen atom is fluorine atom, chlorine atom, bromine atom or iodine atom.

In the substituent R of the formula [I], the expressions such as $C_1$-$C_6$ and the like indicate that the number of carbon atoms of the substituent appearing after the expression is 1 to 6 in the case of $C_1$-$C_6$.

$C_1$-$C_6$ alkyl group indicates, unless otherwise specified, a straight chain or branched chain alkyl group having 1 to 6 carbon atoms. There can be mentioned, for example, groups of methyl, ethyl, n-propyl, isopropyl, n-butyl, sec-butyl, isobutyl, tert-butyl, n-pentyl, 1-methylbutyl, 2-methylbutyl, 3-methylbutyl, 1-ethylpropyl, 1,1-dimethylpropyl, 1,2-dimethylpropyl, neopentyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methylpropyl, 1-ethyl-2-methylpropyl, etc.

Incidentally, the $C_1$-$C_6$ alkyl group may be mono- or polysubstituted by halogen atom, specifically by 1 to 13 halogen atoms.

$C_2$-$C_5$ alkenyl group indicates, unless otherwise specified, a straight chain or branched chain alkenyl group having 2 to 5 carbon atoms. There can be mentioned, for example, groups of vinyl, 1-propenyl, isopropenyl, 2-propenyl, 1-butenyl, 1-methyl-1-propenyl, 2-butenyl, 1-methyl-2-propenyl, 3-butenyl, 2-methyl-1-propenyl, 2-methyl-2-propenyl, 1,3-butadienyl, 1-pentenyl, 1-ethyl-2-propenyl, 2-pentenyl, 1-methyl-1-butenyl, 3-pentenyl, 1-methyl-2-butenyl, 4-pentenyl, 1-methyl-3-butenyl, 3-methyl-1-butenyl, 1,2-dimethyl-2-propenyl, 1,1-dimethyl-2-propenyl, 2-methyl-2-butenyl, 3-methyl-2-butenyl, 1,2,-dimethyl-1-propenyl, 2-methyl-3-butenyl, 3-methyl-3-butenyl, 1,3-pentadienyl, 1-vinyl-2-propenyl, etc.

Incidentally, the $C_2$-$C_5$ alkenyl group may be mono- or poly-substituted by phenyl group, specifically by 1 to 9 phenyl groups.

$C_2$-$C_5$ alkynyl group indicates, unless otherwise specified, a straight chain or branched chain alkynyl group having 2 to 5 carbon atoms. There can be mentioned, for example, groups of ethynyl, 1-propynyl, 2-propynyl, 1-butynyl, 1-methyl-2-propynyl, 2-butynyl, 3-butynyl, 1-pentynyl, 1-ethyl-2-propynyl, 2-pentynyl, 3-pentynyl, 1-methyl-2-butynyl, 4-pentynyl, 1-methyl-3-butynyl, 2-methyl-3-butynyl, etc.

$C_3$-$C_6$ cycloalkyl group indicates, unless otherwise specified, a cycloalkyl group having 3 to 6 carbon atoms. There can be mentioned, for example, groups of cyclopropyl, cyclobutyl, cyclopentyl, cyclohexyl, etc.

In the formula [I], the substituent R may be a phenyl group, or a phenyl group which may be mono- or poly-substituted by same or different substituents selected from the following substituents group α.

[Substituents Group α]

$C_1$-$C_6$ alkyl group, $C_3$-$C_6$ cycloalkyl group, $C_1$-$C_6$ haloalkyl group, phenyl group, halogen atom, cyano group, $C_1$-$C_5$ acyl group, carboxyl group, $C_1$-$C_6$ alkoxycarbonyl group, mono($C_1$-$C_6$ alkyl)carbamoyl group, di($C_1$-$C_6$ alkyl)carbamoyl group, amino group, mono($C_1$-$C_6$ alkyl)amino group, di($C_1$-$C_6$ alkyl)amino group, $C_1$-$C_6$ alkylamide group, $C_1$-$C_6$ alkylsulfonamide group, nitro group, hydroxyl group, $C_1$-$C_6$ alkoxy group, $C_1$-$C_6$ acyloxy group, $C_1$-$C_6$ alkylsulfonyl group, mono($C_1$-$C_6$ alkyl)sulfamoyl group, di($C_1$-$C_6$ alkyl)sulfamoyl group In the above substituents group α, $C_1$-$C_6$ haloalkyl group indicates a straight chain or branched chain alkyl group having 1 to 6 carbon atoms, substituted by halogen atom.

There can be mentioned, for example, groups of fluoromethyl, chloromethyl, bromomethyl, difluoromethyl, dichloromethyl, trifluoromethyl, trichloromethyl, chlorodifluoromethyl, bromodifluoromethyl, 2-fluoroethyl, 1-chloroethyl, 2-chloroethyl, 1-bromoethyl, 2-bromoethyl, 2,2-difluoroethyl, 1,2-dichloroethyl, 2,2-dichloroethyl, 2,2,2-trifluoroethyl, 2,2,2-trichloroethyl, 1,1,2,2-tetrafluoroethyl, pentafluoroethyl, 2-bromo-2-chloroethyl, 2-chloro-1,1,2,2-tetrafluoroethyl, 1-chloro-1,2,2,2-tetrafluoroethyl, 1-chloropropyl, 2-chloropropyl, 3-chloropropyl, 2-bromopropyl, 3-bromopropyl, 2-bromo-1-methylethyl, 3-iodopropyl, 2,3-dichloropropyl, 2,3-dibromopropyl, 3,3,3-trifluoropropyl, 3,3,3-trichloropropyl, 3-bromo-3,3-difluoropropyl, 3,3-dichloro-3-fluoropropyl, 2,2,3,3-tetrafluoropropyl, 1-bromo-3,3,3-trifluoropropyl, 2,2,3,3,3-pentafluoropropyl, 2,2,2-trifluoro-1-trifluoromethylethyl, heptafluoropropyl, 1,2,2,2-tetrafluoro-1-trifluoromethylethyl, 2,3-dichloro-1,1,2,3,3-pentafluoropropyl, 2-chlorobutyl, 3-chlorobutyl, 4-chlorobutyl, 2-chloro-1,1-dimethylethyl, 4-bromobutyl, 3-bromo-2-methylpropyl, 2-bromo-1,1-dimethylethyl, 2,2-dichloro-1,1-dimethylethyl, 2-chloro-1-chloromethyl-2-methylethyl, 4,4,4-trifluorobutyl, 3,3,3-trifluoro-1-methylpropyl, 3,3,3-trifluoro-2-methylpropyl, 2,3,4-trichlorobutyl, 2,2,2-trichloro-1,1-dimethylethyl, 4-chloro-4,4-difluorobutyl, 4,4-dichloro-4-fluorobutyl, 4-bromo-4,4-difluorobutyl, 2,4-dibromo-4,4-difluorobutyl, 3,4-dichloro-3,4,4-trifluorobutyl, 3,3-dichloro-4,4,4-trifluorobutyl, 4-bromo-3,3,4,4-tetrafluorobutyl, 4-bromo-3-chloro-3,4,4-trifluorobutyl, 2,2,3,3,4,4-hexafluorobutyl, 2,2,3,4,4,4-hexafluorobutyl, 2,2,2-trifluoro-1-methyl-1-trifluoromethylethyl, 3,3,3-trifluoro-2-trifluoromethylpropyl, 2,2,3,3,4,4,4-heptafluorobutyl, 2,3,3,3-tetrafluoro-2-trifluoromethylpropyl, 1,1,2,2,3,3,4,4-octafluorobutyl, nona-fluorobutyl, 4-chloro-1,1,2,2,3,3,4,4-octafluorobutyl, 5-fluoropentyl, 5-chloropentyl, 5,5-difluoropentyl, 5,5-dichloropentyl, 5,5,5-trifluoropentyl, 6,6,6-trifluorohexyl, 5,5,6,6,6-pentafluorohexyl, etc.

$C_1$-$C_5$ acyl group indicates a straight chain or branched chain aliphatic acyl group having 1 to 5 carbon atoms. There can be mentioned, for example, groups of formyl, acetyl, propionyl, isopropionyl, butyryl, pivaloyl, etc.

$C_1$-$C_6$ alkoxycarbonyl group indicates a ($C_1$-$C_6$ alkyl)—O—C(=O)— group wherein the alkyl moiety has the above-given definition. There can be mentioned, for example, groups of methoxycarbonyl, ethoxycarbonyl, n-propoxycarbonyl, isopropoxycarbonyl, etc.

Mono($C_1$-$C_6$ alkyl)carbamoyl group indicates a ($C_1$-$C_6$ alkyl)NH—C(=O)— group wherein the alkyl moiety has the above-given definition. There can be mentioned, for example, groups of methylcarbamoyl, ethylcarbamoyl, propylcarbamoyl, etc.

Di($C_1$-$C_6$ alkyl)carbamoyl group indicates a ($C_1$-$C_6$)$_2$N—C(=O)— group wherein the alkyl moiety has the above-given definition. There can be mentioned, for example, groups of dimethylcarbamoyl, diethylcarbamoyl, ethylmethylcarbamoyl, etc.

Mono($C_1$-$C_6$ alkyl)amino group indicates a ($C_1$-$C_6$ alkyl)—NH— group wherein the alkyl moiety has the above-given definition. There can be mentioned, for example, groups of methylamino, ethylamino, etc.

Di($C_1$-$C_6$ alkyl)amino group indicates a ($C_1$-$C_6$ alkyl)$_2$-N— group wherein the alkyl moiety has the above-given definition. There can be mentioned, for example, groups of dimethylamino, diethylamino, methylethylamino, dipropylamino, etc.

$C_1$-$C_6$ alkylamide group indicates a ($C_1$-$C_6$ alkyl)—C(=O)—NH— group wherein the alkyl moiety has the above-given definition. There can be mentioned, for example, groups of methylamide, ethylamide, etc.

$C_1$-$C_6$ alkylsulfonamide group indicates a ($C_1$-$C_6$ alkyl)—SO$_2$—NH— group wherein the alkyl moiety has the above-given definition. There can be mentioned, for example, groups of methylsulfonamide, ethylsulfonamide, etc.

$C_1$-$C_6$ alkoxy group indicates a ($C_1$-$C_6$ alkyl)—O— group wherein the alkyl moiety has the above-given definition. There can be mentioned, for example, groups of methoxy, ethoxy, propoxy, n-propoxy, isopropoxy, butoxy, pentyloxy, hexyloxy, etc.

$C_1$-$C_6$ acyloxy group indicates a straight chain or branched chain aliphatic acyloxy group having 1 to 6 carbon atoms. There can be mentioned, for example, groups of formyloxy, acetyloxy, propionyloxy, isopropionyloxy, etc.

$C_1$-$C_6$ alkylsulfonyl group indicates a ($C_1$-$C_6$ alkyl)—SO$_2$— group wherein the alkyl moiety has the above-given definition. There can be mentioned, for example, groups of metylsulfonyl, ethylsulfonyl, n-propylsulfonyl, etc.

Mono($C_1$-$C_6$ alkyl)sulfamoyl group indicates a ($C_1$-$C_6$ alkyl)—NH—SO$_2$— group wherein the alkyl moiety has the above-given definition. There can be mentioned, for example, groups of methylsulfamoyl, ethylsulfamoyl, propylsulfamoyl, etc.

Di($C_1$-$C_6$ alkyl)sulfamoyl group indicates a ($C_1$-$C_6$ alkyl)$_2$—N—SO$_2$— group wherein the alkyl moiety has the above-given definition. There can be mentioned, for example, groups of dimethylsulfamoyl, diethylsulfamoyl, methylethylsulfamoyl, dipropylsulfamoyl, etc.

In the substituent R of the formula [I], the heterocyclic group is a 5- to 10-membered heterocyclic group containing at least one of oxygen atom, sulfur atom and nitrogen atom. There can be mentioned, for example, groups of pyridine, pyrrole, furan, thiophene, oxazole, thiazole, imidazole, isoxazole, isothiazole, pyrazole, 1,2,3-oxadiazole, 1,2,3-thiadiazole, 1,2,3-triazole, 1,2,4-oxadiazole, 1,2,4-thiadiazole, 1,2,4-triazole, 1,2,5-oxadiazole, 1,2,5-thiadiazole, indole, benzofuran, benzothiophene, benzoxazole, benzothiazole, benzoimidazole, benzoisoxazole, benzoisothiazole, indazole, 1,2,3-benzoxadiazole, 1,2,3-benzothiadiazole, benzotriazole, 2,1,3-benzoxadiazole, 2,1,3-benzothiadiazole, etc.

Next, specific examples of the present invention compound represented by the general formula [I] are shown in Table 1 to Table 10. However, the present invention compound is in no way restricted to them.

In the tables of the present Description, the following expressions indicate the following groups, respectively.

For example, Me indicates methyl group; Et indicates ethyl group; Pr-n indicates n-propyl group; Pr-i indicates isopropyl group; Pr-c indicates cyclopropyl group; Bu-n indicates n-butyl group; Bu-s indicates secondary butyl group; Bu-i indicates isobutyl group; Bu-t indicates tertiary butyl group; and Ph indicates phenyl group. Also, for example, 2-OMe indicates methoxy group which is substituted at the 2-position; and 2,6-$Cl_2$ indicates chlorine group which is substituted at the 2-position and the 6-position.

Incidentally, some compound Nos. in the tables are referred to in the description following the tables.

TABLE 1

| Compound No. | $X^1$ | $X^2$ | A | R |
| --- | --- | --- | --- | --- |
| I-1 | Cl | Cl | O | Me |
| I-2 | Cl | Br | O | Me |
| I-3 | Br | Cl | O | Me |
| I-4 | Br | Br | O | Me |
| I-5 | Cl | Cl | O | Et |
| I-6 | Cl | Cl | O | Pr |
| I-7 | Cl | Cl | O | Pr-i |
| I-8 | Cl | Cl | O | Pr-c |
| I-9 | Cl | Cl | O | Bu |
| I-10 | Cl | Cl | O | Bu-i |
| I-11 | Cl | Cl | O | Bu-s |
| I-12 | Cl | Cl | O | Bu-t |
| I-13 | Cl | Cl | O | $CHF_2$ |
| I-14 | Cl | Cl | O | $CF_3$ |
| I-15 | Cl | Cl | O | $CH_2CF_3$ |
| I-16 | Cl | Cl | O | $C_2F_5$ |
| I-17 | Cl | Cl | O | $CH_2CH_2Cl$ |
| I-18 | Cl | Cl | O | $CH_2CH_2CF_3$ |
| I-19 | Cl | Cl | O | $CH_2CH_2CH_2Cl$ |
| I-20 | Cl | Cl | O | $CF(CF_3)_2$ |
| I-21 | Cl | Cl | O | CH=$CH_2$ |
| I-22 | Cl | Cl | O | CH=CHMe |
| I-23 | Cl | Cl | O | CH=CHPh |
| I-24 | Cl | Cl | O | CH=CHCH=CHMe |
| I-25 | Cl | Cl | O | C≡CH |
| I-26 | Cl | Cl | O | C≡CMe |
| I-27 | Cl | Cl | O | C≡CC≡CMe |
| I-28 | Cl | Cl | S | Me |
| I-29 | Cl | Cl | S | Et |
| I-30 | Cl | Cl | S | Pr |
| I-31 | Cl | Cl | S | Pr-i |
| I-32 | Cl | Cl | S | Pr-c |
| I-33 | Cl | Cl | S | Bu |

TABLE 2

| Compound No. | $X^1$ | $X^2$ | A | R |
| --- | --- | --- | --- | --- |
| I-34 | Cl | Cl | S | Bu-i |
| I-35 | Cl | Cl | S | Bu-s |
| I-36 | Cl | Cl | S | Bu-t |
| I-37 | Cl | Cl | S | $CHF_2$ |
| I-38 | Cl | Cl | S | $CF_3$ |
| I-39 | Cl | Cl | S | $CH_2CF_3$ |

TABLE 2-continued

| Compound No. | X$^1$ | X$^2$ | A | R |
|---|---|---|---|---|
| I-40 | Cl | Cl | S | C$_2$F$_5$ |
| I-41 | Cl | Cl | S | CH$_2$CH$_2$Cl |
| I-42 | Cl | Cl | S | CH$_2$CH$_2$CF$_3$ |
| I-43 | Cl | Cl | S | CH$_2$CH$_2$CH$_2$Cl |
| I-44 | Cl | Cl | S | CF(CF$_3$)$_2$ |
| I-45 | Cl | Cl | S | CH=CH$_2$ |
| I-46 | Cl | Cl | S | CH=CHMe |
| I-47 | Cl | Cl | S | CH=CHPh |
| I-48 | Cl | Cl | S | CH=CHCH=CHMe |
| I-49 | Cl | Br | S | CH=CHCH=CHMe |
| I-50 | Br | Cl | S | CH=CHCH=CHMe |
| I-51 | Br | Br | S | CH=CHCH=CHMe |
| I-52 | Cl | Cl | S | C≡CH |
| I-53 | Cl | Cl | S | C≡CMe |
| I-54 | Cl | Cl | S | C≡CC≡CMe |

TABLE 3

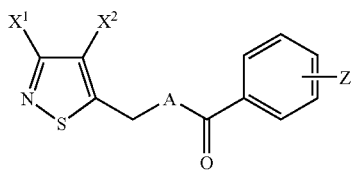

| Compound No. | X$^1$ | X$^2$ | A | Z |
|---|---|---|---|---|
| II-1 | Cl | Cl | O | H |
| II-2 | Cl | Br | O | H |
| II-3 | Br | Cl | O | H |
| II-4 | Br | Br | O | H |
| II-5 | Cl | Cl | O | 2-Me |
| II-6 | Cl | Cl | O | 3-Et |
| II-7 | Cl | Cl | O | 4-Pr |
| II-8 | Cl | Cl | O | 2-Pr-i |
| II-9 | Cl | Cl | O | 2-Pr-c |
| II-10 | Cl | Cl | O | 3-CF$_3$ |
| II-11 | Cl | Cl | O | 4-CF(CF$_3$)$_2$ |
| II-12 | Cl | Cl | O | 2-Ph |
| II-13 | Cl | Cl | O | 2-F |
| II-14 | Cl | Cl | O | 2-Cl |
| II-15 | Cl | Cl | O | 2-Br |
| II-16 | Cl | Cl | O | 2-I |
| II-17 | Cl | Cl | O | 2-CN |
| II-18 | Cl | Cl | O | 2-COMe |
| II-19 | Cl | Cl | O | 3-COEt |
| II-20 | Cl | Cl | O | 3-COPr |
| II-21 | Cl | Cl | O | 4-COPr-i |
| II-22 | Cl | Cl | O | 4-COBu-t |
| II-23 | Cl | Cl | O | 2-COOH |
| II-24 | Cl | Cl | O | 2-COOMe |
| II-25 | Cl | Cl | O | 3-COOEt |
| II-26 | Cl | Cl | O | 3-COOPr |
| II-27 | Cl | Cl | O | 4-COOPr-i |
| II-28 | Cl | Cl | O | 4-COOBu-t |
| II-29 | Cl | Cl | O | 2-CONHMe |
| II-30 | Cl | Cl | O | 3-CONHEt |
| II-31 | Cl | Cl | O | 2-CONHPr |
| II-32 | Cl | Cl | O | 2-CONHPr-i |

TABLE 4

| Compound No. | X$^1$ | X$^2$ | A | Z |
|---|---|---|---|---|
| II-33 | Cl | Cl | O | 2-CONMe$_2$ |
| II-34 | Cl | Cl | O | 3-CONEt$_2$ |
| II-35 | Cl | Cl | O | 4-CONPr$_2$ |
| II-36 | Cl | Cl | O | 2-CON(Pr-i)$_2$ |
| II-37 | Cl | Cl | O | 2-NH$_2$ |
| II-38 | Cl | Cl | O | 3-NHMe |
| II-39 | Cl | Cl | O | 4-NHEt |

TABLE 4-continued

| Compound No. | X$^1$ | X$^2$ | A | Z |
|---|---|---|---|---|
| II-40 | Cl | Cl | O | 2-NHPr |
| II-41 | Cl | Cl | O | 2-NHPr-i |
| II-42 | Cl | Cl | O | 2-NMe$_2$ |
| II-43 | Cl | Cl | O | 3-NEt$_2$ |
| II-44 | Cl | Cl | O | 4-NPr$_2$ |
| II-45 | Cl | Cl | O | 2-N(Pr-i)$_2$ |
| II-46 | Cl | Cl | O | 2-NHCOMe |
| II-47 | Cl | Cl | O | 3-NHCOEt |
| II-48 | Cl | Cl | O | 4-NHCOPr |
| II-49 | Cl | Cl | O | 2-NHCOPr-i |
| II-50 | Cl | Cl | O | 2-NHCOBu-t |
| II-51 | Cl | Cl | O | 2-NHSO$_2$Me |
| II-52 | Cl | Cl | O | 3-NHSO$_2$Et |
| II-53 | Cl | Cl | O | 4-NHSO$_2$Pr |
| II-54 | Cl | Cl | O | 2-NHSO$_2$Pr-i |
| II-55 | Cl | Cl | O | 2-NO$_2$ |
| II-56 | Cl | Cl | O | 2-OH |
| II-57 | Cl | Cl | O | 2-OMe |
| II-58 | Cl | Cl | O | 3-OEt |
| II-59 | Cl | Cl | O | 4-OPr |
| II-60 | Cl | Cl | O | 2-OPr-i |
| II-61 | Cl | Cl | O | 2-OCOMe |
| II-62 | Cl | Cl | O | 3-OCOEt |
| II-63 | Cl | Cl | O | 4-OCOPr |
| II-64 | Cl | Cl | O | 2-OCOPr-i |
| II-65 | Cl | Cl | O | 2-OCOBu-t |
| II-66 | Cl | Cl | O | 2-SO$_2$Me |
| II-67 | Cl | Cl | O | 3-SO$_2$Et |
| II-68 | Cl | Cl | O | 4-SO$_2$Pr |
| II-69 | Cl | Cl | O | 2-SO$_2$Pr-i |
| II-70 | Cl | Cl | O | 2-SO$_2$NHMe |

TABLE 5

| Compound No. | X$^1$ | X$^2$ | A | Z |
|---|---|---|---|---|
| II-71 | Cl | Cl | O | 3-SO$_2$NHEt |
| II-72 | Cl | Cl | O | 4-SO$_2$NHPr |
| II-73 | Cl | Cl | O | 2-SO$_2$NHPr-i |
| II-74 | Cl | Cl | O | 2-SO$_2$NMe$_2$ |
| II-75 | Cl | Cl | O | 3-SO$_2$NEt$_2$ |
| II-76 | Cl | Cl | O | 4-SO$_2$NPr$_2$ |
| II-77 | Cl | Cl | O | 2,6-Me$_2$ |
| II-78 | Cl | Cl | O | 2,6-Cl$_2$ |
| II-79 | Cl | Cl | O | 2,6-(OMe)$_2$ |
| II-80 | Cl | Cl | O | 2,6-(NO$_2$)$_2$ |
| II-81 | Cl | Cl | O | 2,6-(CN)$_2$ |
| II-82 | Cl | Cl | O | 2-NO$_2$, 6-Me |
| II-83 | Cl | Cl | O | 2-NO$_2$, 6-COOMe |
| II-84 | Cl | Cl | S | H |
| II-85 | Cl | Br | S | H |
| II-86 | Br | Cl | S | H |
| II-87 | Br | Br | S | H |
| II-88 | Cl | Cl | S | 2-Me |
| II-89 | Cl | Cl | S | 3-Et |
| II-90 | Cl | Cl | S | 4-Pr |
| II-91 | Cl | Cl | S | 2-Pr-i |
| II-92 | Cl | Cl | S | 2-Pr-c |
| II-93 | Cl | Cl | S | 3-CF$_3$ |
| II-94 | Cl | Cl | S | 4-CF(CF$_3$)$_2$ |
| II-95 | Cl | Cl | S | 2-Ph |
| II-96 | Cl | Cl | S | 2-F |
| II-97 | Cl | Cl | S | 2-Cl |
| II-98 | Cl | Cl | S | 2-Br |
| II-99 | Cl | Cl | S | 2-I |
| II-100 | Cl | Cl | S | 2-CN |
| II-101 | Cl | Cl | S | 2-COMe |
| II-102 | Cl | Cl | S | 3-COEt |
| II-103 | Cl | Cl | S | 3-COPr |
| II-104 | Cl | Cl | S | 4-COPr-i |
| II-105 | Cl | Cl | S | 4-COBu-t |
| II-106 | Cl | Cl | S | 2-COOH |
| II-107 | Cl | Cl | S | 2-COOMe |
| II-108 | Cl | Cl | S | 3-COOEt |

TABLE 6

| Compound No. | X¹ | X² | A | Z |
|---|---|---|---|---|
| II-109 | Cl | Cl | S | 3-COOPr |
| II-110 | Cl | Cl | S | 4-COOPr-i |
| II-111 | Cl | Cl | S | 4-COOBu-t |
| II-112 | Cl | Cl | S | 2-CONHMe |
| II-113 | Cl | Cl | S | 3-CONHEt |
| II-114 | Cl | Cl | S | 2-CONHPr |
| II-115 | Cl | Cl | S | 2-CONHPr-i |
| II-116 | Cl | Cl | S | 2-CONMe₂ |
| II-117 | Cl | Cl | S | 3-CONEt₂ |
| II-118 | Cl | Cl | S | 4-CONPr₂ |
| II-119 | Cl | Cl | S | 2-CON(Pr-i)₂ |
| II-120 | Cl | Cl | S | 2-NH₂ |
| II-121 | Cl | Cl | S | 3-NHMe |
| II-122 | Cl | Cl | S | 4-NHEt |
| II-123 | Cl | Cl | S | 2-NHPr |
| II-124 | Cl | Cl | S | 2-NHPr-i |
| II-125 | Cl | Cl | S | 2-NMe₂ |
| II-126 | Cl | Cl | S | 3-NEt₂ |
| II-127 | Cl | Cl | S | 4-NPr₂ |
| II-128 | Cl | Cl | S | 2-N(Pr-i)₂ |
| II-129 | Cl | Cl | S | 2-NHCOMe |
| II-130 | Cl | Cl | S | 3-NHCOEt |
| II-131 | Cl | Cl | S | 4-NHCOPr |
| II-132 | Cl | Cl | S | 2-NHCOPr-i |
| II-133 | Cl | Cl | S | 2-NHCOBu-t |
| II-134 | Cl | Cl | S | 2-NHSO₂Me |
| II-135 | Cl | Cl | S | 3-NHSO₂Et |
| II-136 | Cl | Cl | S | 4-NHSO₂Pr |
| II-137 | Cl | Cl | S | 2-NHSO₂Pr-i |
| II-138 | Cl | Cl | S | 2-NO₂ |
| II-139 | Cl | Cl | S | 2-OH |
| II-140 | Cl | Cl | S | 2-OMe |
| II-141 | Cl | Cl | S | 3-OEt |
| II-142 | Cl | Cl | S | 4-OPr |
| II-143 | Cl | Cl | S | 2-OPr-i |
| II-144 | Cl | Cl | S | 2-OCOMe |
| II-145 | Cl | Cl | S | 3-OCOEt |
| II-146 | Cl | Cl | S | 4-OCOPr |

TABLE 7

| Compound No. | X¹ | X² | A | Z |
|---|---|---|---|---|
| II-147 | Cl | Cl | S | 2-OCOPr-i |
| II-148 | Cl | Cl | S | 2-OCOBu-t |
| II-149 | Cl | Cl | S | 2-SO₂Me |
| II-150 | Cl | Cl | S | 3-SO₂Et |
| II-151 | Cl | Cl | S | 4-SO₂Pr |
| II-152 | Cl | Cl | S | 2-SO₂Pr-i |
| II-153 | Cl | Cl | S | 2-SO₂NHMe |
| II-154 | Cl | Cl | S | 3-SO₂NHEt |
| II-155 | Cl | Cl | S | 4-SO₂NHPr |
| II-156 | Cl | Cl | S | 2-SO₂NHPr-i |
| II-157 | Cl | Cl | S | 2-SO₂NMe₂ |
| II-158 | Cl | Cl | S | 3-SO₂NEt₂ |
| II-159 | Cl | Cl | S | 4-SO₂NPr₂ |
| II-160 | Cl | Cl | S | 2-SO₂N(Pr-i)₂ |
| II-161 | Cl | Cl | S | 2,6-Cl₂ |
| II-162 | Cl | Cl | S | 2,6-(OMe)₂ |
| II-163 | Cl | Cl | S | 2,6-(NO₂)₂ |
| II-164 | Cl | Cl | S | 2,6-(CN)₂ |
| II-165 | Cl | Cl | S | 2-NO₂, 6-Me |
| II-166 | Cl | Cl | S | 2-NO₂, 6-COOMe |

TABLE 8

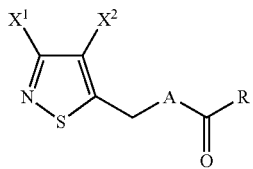

| Compound No. | X¹ | X² | A | R |
|---|---|---|---|---|
| III-1 | Cl | Cl | O | 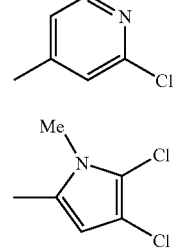 |
| III-2 | Cl | Cl | O | 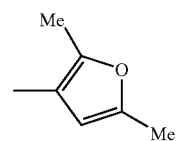 |
| III-3 | Cl | Cl | O | 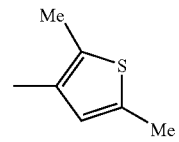 |
| III-4 | Cl | Cl | O | 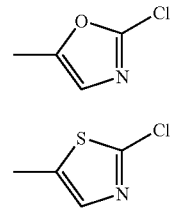 |
| III-5 | Cl | Cl | O | 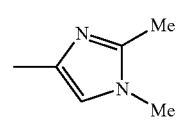 |
| III-6 | Cl | Cl | O | 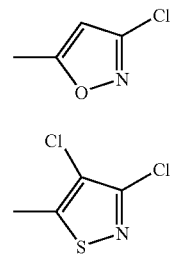 |
| III-7 | Cl | Cl | O | 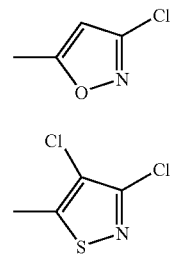 |
| III-8 | Cl | Cl | O | 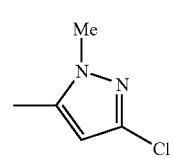 |
| III-9 | Cl | Cl | O | |
| III-10 | Cl | Cl | O | |

TABLE 8-continued

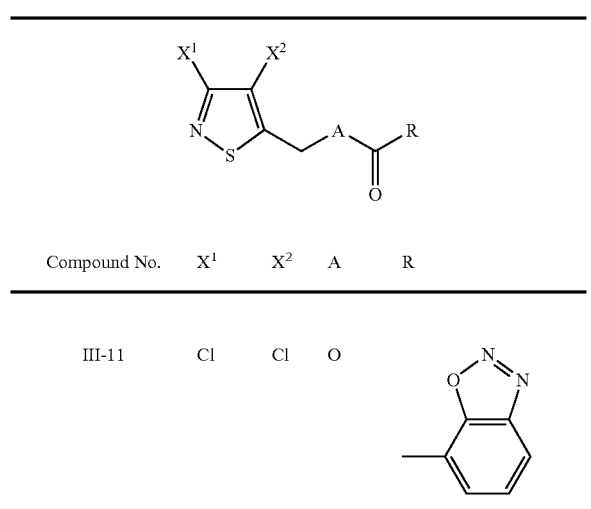

| Compound No. | X¹ | X² | A | R |
|---|---|---|---|---|
| III-11 | Cl | Cl | O | (4-methyl-2,1,3-benzoxadiazol-?) |

TABLE 9

| Compound No. | X¹ | X² | A | R |
|---|---|---|---|---|
| III-12 | Cl | Cl | O | (5-methyl-4-chloro-1,2,3-thiadiazol-?) |
| III-13 | Cl | Cl | O | (1,4-dimethyl-5-chloro-1,2,3-triazol-?) |
| III-14 | Cl | Cl | O | (5-methyl-3-chloro-1,2,4-oxadiazol-?) |
| III-15 | Cl | Cl | O | (5-methyl-3-chloro-1,3,4-thiadiazol-?) |
| III-16 | Cl | Cl | O | (1,5-dimethyl-3-chloro-1,2,4-triazol-?) |
| III-17 | Cl | Cl | O | (4-methyl-3-chloro-furazan-?) |
| III-18 | Cl | Cl | O | (4-methyl-3-chloro-1,2,5-thiadiazol-?) |

TABLE 9-continued

| Compound No. | X¹ | X² | A | R |
|---|---|---|---|---|
| III-19 | Cl | Cl | O | (1,7-dimethyl-2-chloro-indol-?) |
| III-20 | Cl | Cl | O | (2,7-dimethyl-benzofuran-?) |
| III-21 | Cl | Cl | O | (2,7-dimethyl-benzothiophen-?) |
| III-22 | Cl | Cl | O | (7-methyl-2-chloro-benzoxazol-?) |
| III-23 | Cl | Cl | O | (7-methyl-2-chloro-benzothiazol-?) |
| III-24 | Cl | Cl | O | (1,7-dimethyl-benzimidazol-?) |

TABLE 10

| Compound No. | X¹ | X² | A | R |
|---|---|---|---|---|
| III-25 | Cl | Cl | O |  |

TABLE 10-continued

| Compound No. | $X^1$ | $X^2$ | A | R |
|---|---|---|---|---|
| III-26 | Cl | Cl | O | 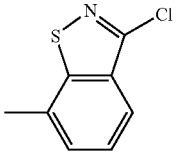 |
| III-27 | Cl | Cl | O | 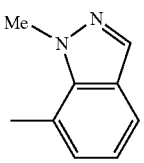 |
| III-28 | Cl | Cl | O | 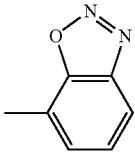 |
| III-29 | Cl | Cl | O | 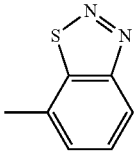 |
| III-30 | Cl | Cl | O | 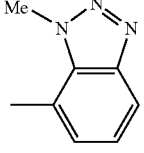 |
| III-31 | Cl | Cl | O | 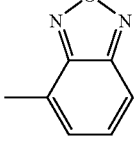 |
| III-32 | Cl | Cl | O | 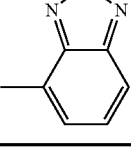 |

Representative processes for producing the present invention compound are shown below. However, the process for producing the present invention compound is not restricted to these processes.

[Formula 2]

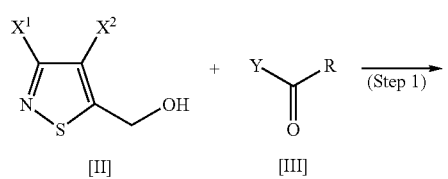

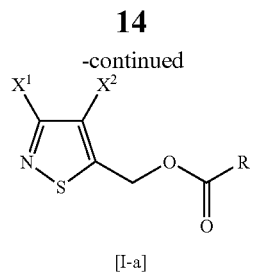

(wherein $X^1$, $X^2$ and R have the same definitions as given above, and Y is halogen atom or hydroxyl group.)

(Step 1)

The compound represented by the general formula [I-a] can be produced by reacting an alcohol represented by the general formula [II] with a carboxylic acid or carboxylic acid halide represented by the general formula [III] in the presence or absence of a base, or in the presence or absence of a condensation agent, in a solvent or in the absence of a solvent.

The use amount of the compound represented by the general formula [III] is appropriately selected in a range of 0.8 to 2.0 mols relative to 1 mol of the compound represented by the general formula [II], and is preferably 1.0 to 1.2 mols.

As the base usable in the present step, there can be mentioned, for example, metal carbonates such as sodium carbonate, potassium carbonate and the like; metal bicarbonates such as sodium bicarbonate, potassium bicarbonate and the like; carboxylic acid salts such as sodium acetate, potassium acetate and the like; metal alkoxides such as sodium methoxide, sodium ethoxide, potassium tert-butoxide and the like; metal hydroxides such as sodium hydroxide, potassium hydroxide, calcium hydroxide and the like; metal hydrides such as sodium hydride, potassium hydride, calcium hydride and the like; and organic bases such as triethylamine N,N-diisopropylethylamine, pyridine, 1,8-diazabicyclo[5.4.0]undec-7-ene (DBU) and the like.

The use amount of the base is appropriately selected in a range of 0 to 10 mols relative to 1 mol of the compound represented by the general formula [II], and is preferably 0 to 1.2 mols.

The solvent usable in the present step may be any solvent as long as it does not inhibit the progress of the present reaction. There can be used, for example, ethers such as diethyl ether, tetrahydrofuran, dioxane, monoglyme, diglyme and the like; halogenated hydrocarbons such as dichloromethane, chloroform, carbon tetrachloride, dichloroethane and the like; aromatic hydrocarbons such as benzene, chlorobenzene, nitrobenzene, toluene and the like; amides such as N,N-dimethylformamide, N,N-dimethylacetamide and the like; ureas such as 1,3-dimethyl-2-imidazolinone and the like; sulfur compounds such as dimethyl sulfoxide and the like; and nitrites such as acetonitrile and the like. Mixed solvents thereof may be used as well.

The use amount of the solvent is 0 to 100 liters, preferably 0.5 to 2.0 liters relative to 1 mol of the compound represented by the general formula [II].

As the condensation agent usable in the present step, there can be mentioned carbodiimides such as carbonyldiimidazole (CDI), dicyclohexylcarbodiimide (DCC) and the like; benzotriazol-1-yloxytris(diethylamino)phosphonium hexafluorophosphonate (BOP reagent); etc.

The use amount of the condensation agent is appropriately selected in a range of 0 to 10 mols relative to 1 mol of the compound represented by the general formula [II], and is preferably 0 to 1.2 mols.

The reaction temperature is selected in a range from −20° C. to the boiling point of the inert solvent used, and is preferably 0° C. to 100° C.

The reaction time varies depending upon the reaction temperature, the reaction substrate, the scale of reaction, etc. but is ordinarily 30 minutes to 48 hours.

After the completion of the reaction, the present invention compound represented by the general formula [I], which is an objective substance of the present step, is obtained from the reaction system according to an ordinary method. The present invention compound obtained may be as necessary purified by an operation such as column chromatography, recrystallization or the like.

The compound represented by the general formula [III], used in the present step is produced by an ordinary process or may be a commercial reagent which is used per se.

The compound represented by the general formula [II], used in the present step, can be produced by the following process.

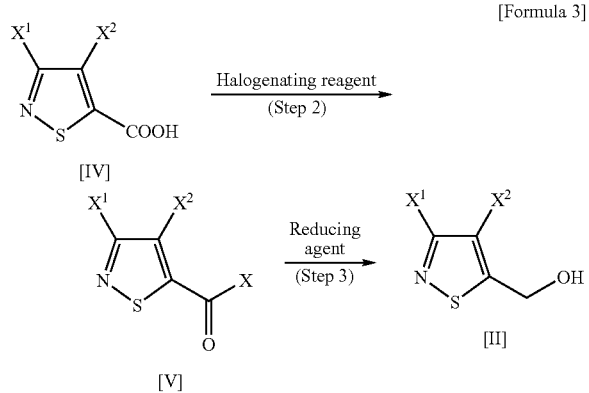

[Formula 3]

(wherein $X^1$ and $X^2$ have the same definitions as given above, and X is a halogen atom.)

(Step 2)

The compound represented by the general formula [V] can be produced by reacting a compound represented by the general formula [IV] with a halogenating reagent in a solvent or in the absence of a solvent.

As the halogenating reagent usable in the present step, there can be mentioned, for example, acid chlorides such as oxalyl chloride, thionyl chloride and the like. As necessary, an amide such as N,N-dimethylformamide (DMF) or the like may be added in a catalytic amount.

The use amount of the halogenating agent is appropriately selected in a range of 1 to 100 mols relative to 1 mol of the compound represented by the general formula [IV] and is preferably 1 to 5 mols.

The solvent usable in the present step may be any solvent as long as it does not inhibit the progress of the present reaction. There can be used, for example, ethers such as diethyl ether, tetrahydrofuran (THF), dioxane, monoglyme, diglyme and the like; halogenated hydrocarbons such as dichloromethane, chloroform, carbon tetrachloride, dichloroethane and the like; aromatic hydrocarbons such as benzene, chlorobenzene, nitrobenzene, toluene and the like; and nitriles such as acetonitrile and the like. Mixed solvents thereof may be used as well.

The use amount of the solvent is 0 to 100 liters, preferably 0 to 2.0 liters relative to 1 mol of the compound represented by the general formula [IV].

The reaction temperature is selected in a range from −20° C. to the boiling point of the inert solvent used, and is preferably 0° C. to 100° C.

The reaction time differs depending upon the reaction temperature, the reaction substrate, the scale of reaction, etc., but is ordinarily 30 minutes to 10 hours.

After the completion of the reaction, the compound represented by the general formula [V], which is an objective substance of the present step, is obtained from the reaction system according to an ordinary method. The obtained compound of the general formula [V] may be as necessary purified by an operation such as column chromatography, recrystallization or the like.

(Step 3)

The compound represented by the general formula [II] can be produced by reacting a compound represented by the general formula [V] with a reducing agent in a solvent or in the absence of a solvent.

As the reducing agent usable in the present step, there can be mentioned, for example, boron hydride compounds such as sodium borohydride and the like.

The use amount of the reducing agent is appropriately selected in a range of 1 to 100 mols relative to 1 mol of the compound represented by the general formula [V] and is preferably 1 to 5 mols.

The solvent usable in the present step may be any solvent as long as it does not inhibit the progress of the present reaction. There can be used, for example, ethers such as diethyl ether, tetrahydrofuran, dioxane, monoglyme, diglyme and the like; alcohols such as methanol, ethanol, propanol, isopropanol, butanol, tert-butanol and the like; halogenated hydrocarbons such as dichloromethane, chloroform, carbon tetrachloride, dichloroethane and the like; aromatic hydrocarbons such as benzene, chlorobenzene, nitrobenzene, toluene and the like; amides such as N,N-dimethylformamide, N,N-dimethylacetamide and the like; ureas such as 1,3-dimethyl-2-imidazolinone and the like; sulfur compounds such as dimethyl sulfoxide and the like; nitrites such as acetonitrile and the like; and water. Mixed solvents thereof may be used as well.

The use amount of the solvent is 0 to 100 liters, preferably 0.1 to 2.0 liters relative to 1 mol of the compound represented by the general formula [V].

The reaction temperature is selected in a range from −20° C. to the boiling point of the inert solvent used, and is preferably 0° C. to 100° C.

The reaction time differs depending upon the reaction temperature, the reaction substrate, the scale of reaction, etc., but is ordinarily 10 minutes to 10 hours.

After the completion of the reaction, the compound represented by the general formula [II], which is an objective substance of the present step, is obtained from the reaction system according to an ordinary method. The obtained compound of the general formula [II] may be as necessary purified by an operation such as column chromatography, recrystallization or the like.

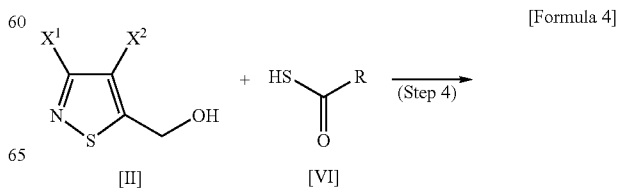

[Formula 4]

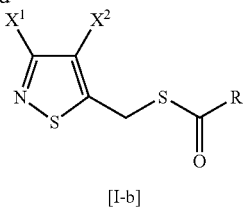

[I-b]

(wherein $X^1$, $X^2$ and R have the same definitions as given above.)

(Step 4)

The compound represented by the general formula [I-b] can be produced by reacting an alcohol represented by the general formula [II] with a thiocarboxylic acid represented by the general formula [VI] in the presence of a phosphine and an azodicarboxylic acid ester in a solvent or in the absence of a solvent.

The use amount of the compound represented by the general formula [VI] is appropriately selected in a range of 1 to 10 mols relative to 1 mol of the compound represented by the general formula [II], and is preferably 1.0 to 2.0 mols.

As the phosphine usable in the present step, there can be mentioned, for example, triarylphosphines such as triphenylphosphine and the like; and trialkylphosphines such as tributylphosphine and the like.

The use amount of the phosphine is appropriately selected in a range of 1 to 10 mols relative to 1 mol of the compound represented by the general formula [II], and is preferably 1.0 to 1.5 mols.

As the azodicarboxylic acid ester usable in the present step, there can be mentioned, for example, diethyl azodicarboxylate and diisopropyl azodicarboxylate.

The use amount of the azodicarboxylic acid ester is appropriately selected in a range of 1 to 10 mols relative to 1 mol of the compound represented by the general formula [II], and is preferably 1.0 to 1.5 mols.

The solvent usable in the present step may be any solvent as long as it does not inhibit the progress of the present reaction. There can be used, for example, ethers such as diethyl ether, tetrahydrofuran, dioxane, monoglyme, diglyme and the like; halogenated hydrocarbons such as dichloromethane, chloroform, carbon tetrachloride, dichloroethane and the like; aromatic hydrocarbons such as benzene, chlorobenzene, nitrobenzene, toluene and the like; amides such as N,N-dimethylformamide, N,N-dimethylacetamide and the like; ureas such as 1,3-dimethyl-2-imidazolinone and the like; sulfur compounds such as dimethyl sulfoxide and the like; and nitrites such as acetonitrile and the like. Mixed solvents thereof may be used as well.

The use amount of the solvent is 0 to 100 liters, preferably 0.1 to 2.0 liters relative to 1 mol of the compound represented by the general formula [II].

The reaction temperature is selected in a range from −50° C. to the boiling point of the inert solvent used, and is preferably 0° C. to 50° C.

The reaction time differs depending upon the reaction temperature, the reaction substrate, the scale of reaction, etc., but is ordinarily 30 minutes to 48 hours.

After the completion of the reaction, the present invention compound represented by the general formula [I-b], which is an objective substance of the reaction, is obtained from the reaction system according to an ordinary method. The present invention compound obtained may be as necessary purified by an operation such as column chromatography, recrystallization or the like.

The compound represented by the general formula [VI], used in the present step is produced by an ordinary process or may be a commercial reagent which is used per se.

Meanwhile, the agricultural or horticultural plant disease-controlling agent of the present invention contains, as an active ingredient, a 3,4-dihalogenoisothiazole derivative represented by the general formula [I] or a salt thereof.

Incidentally, as the salt of the 3,4-dihalogenoisothiazole derivative represented by the general formula [I], there can be mentioned alkali metal salts such as sodium salt, potassium salt and the like; salts of alkaline earth metals such as calcium and the like; salts of amines such as ammonia, triethylamine, diisopropylamine and the like; and salts of organic sulfonic acids such as methanesulfonic acid, p-toluenesulfonic acid and the like.

The plant diseases to which the agricultural or horticultural plant disease-controlling agent of the present invention shows a controlling effect, are shown below non-restrictively.

*Pseudoperonospora cubensis, Venturia inaequalis, Sphaerotheca cucurbitae, Erysiphe graminis, Stagonospra nodorum, Pyricularia oryzae, Botrytis cinerea, Rhizoctonia solani, Puccinia recondita, Pseudomonas syringae, Xanthomonas oryzae, Burkholderia glumae, Burkholderia plantarii, Acidovorax avenae, Erwinia ananas, Colletotrichum orbiculare.*

The agricultural or horticultural plant disease-controlling agent of the present invention may be a present invention compound or a salt thereof per se. However, it may contain, as necessary, additive components ordinarily used in agricultural chemicals.

As the additive components, there can be mentioned a carrier such as solid carrier, liquid carrier or the like; a surfactant; a binder or a tackifier; a thickener; a coloring agent; a spreader; a sticker; an antifreezing agent; an anti-caking agent; a collapsing agent; a decomposition inhibitor; etc. As necessary, there may be further used additive components such as antiseptic agent, a piece of plant and the like. These additive components may be used singly or in combination of two or more kinds.

The above additive components are explained. As the solid carrier, there can be mentioned, for example, natural minerals such as quartz, clay, kaolinite, pyrophillite, sericite, talc, bentonite, acid clay, attapulgite, zeolite, diatomaceous earth and the like; inorganic salts such as calcium carbonate, ammonium sulfate, sodium sulfate, potassium chloride and the like; organic solid carriers such as synthetic silicic acid, synthetic silicic acid salt, starch, cellulose, plant powder and the like; plastic carriers such as polyethylene, polypropylene, polyvinylidene chloride and the like; urea; inorganic hollow materials; plastic hollow materials; and fumed silica (fumed silica, white carbon). These may be used singly or in combination of two or more kinds.

As the liquid carrier, there can be mentioned, for example, alcohols such as monohydric alcohol (e.g. methanol, ethanol, propanol, isopropanol or butanol) and polyhydric alcohol (e.g. ethylene glycol, diethylene glycol, propylene glycol, hexylene glycol, polyethylene glycol, polypropylene glycol or glycerine); polyhydric alcohol compounds such as propylene glycol ether and the like; ketones such as acetone, methyl ethyl ketone, methyl isobutyl ketone, diisobutyl ketone, cyclohexanone and the like; ethers such as ethyl ether, dioxane, ethylene glycol monoethyl ether, dipropyl ether, tetrahydrofuran and the like; aliphatic hydrocarbons such as normal paraffin, naphthene, isoparaffin, kerosene, mineral oil and the like; aromatic hydrocarbons such as benzene, toluene, xylene, solvent naphtha, alkylnaphthalene and the like; halogenated hydrocarbons such as dichloromethane, chloroform, carbon tetrachloride and the like; esters such as ethyl acetate, diisopropyl phthalate, dibutyl phthalate, dioctyl phthalate, dimethyl adipate and the like; lactones such as γ-butyrolactone and the like; amides such as dimethylformamide, diethylformamide, dimethylacetamide, N-alkylpyrrolidinone and the like; nitriles such as acetonitrile and the like; sulfur compounds such as dimethyl sulfoxide and the like; plant oils such as soybean oil, rape oil, cotton seed oil, castor oil and the like; and water. These may be used singly or in combination of two or more kinds.

As the surfactant, there can be mentioned, for example, nonionic surfactants such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkylether, polyoxyethylene alkylphenylether, polyoxyethylene dialkylphenylether, polyoxyethylene alkylphenylether formaldehyde condensate, polyoxyethylene polyoxypropylene block copolymer, alkylpolyoxyethylene polypropylene block copolymer ether, polyoxyethylene alkylamine, polyoxyethylene fatty acid amide, polyoxyethylene fatty acid bisphenylether, polyalkylene benzylphenyl ether, polyoxyalkylene styrylphenyl ether, acetylene diol, polyoxyalkylene-added acetylene diol, polyoxyethylene ether silicone, ester silicone, fluorochemical surfactant, polyoxyethylene castor oil and polyoxyethylene hydrogenated castor oil and the like; anionic surfactants such as alkyl sulfate, polyoxyethylene alkylether sulfate, polyoxyethylene alkylphenylether sulfate, polyoxyethylene styrylphenyl ether sulfate, alkyl benzene sulfonate, lignin sulfonate, alkyl sulfosuccinate, naphthalene sulfonate, alkyl naphthalene sulfonate, naphthalenesulfonic acid formaldehyde condensate salt, alkylnaphthalenesulfonic acid formaldehyde condensate salt, fatty acid salt, polycarboxylate, N-methyl-fatty acid sarcosinate, resinate, polyoxyethylene alkylether phosphate, polyoxyethylene alkylphenylether phosphate, salt of alcohol sulfate, dinaphthyl methanesulfonate and the like; cationic surfactants such as laurylamine hydrochloride, stearylamine hydrochloride, oleylamine hydrochloride, stearylamine acetate, stearoylamino-propylamine acetate, alkyltrimethylammonium chloride, alkyldimethylbenzalkonium chloride and the like; and amphoteric surfactants of amino acid type, betaine type or other type.

These surfactants may be used singly or in combination of two or more kinds.

As the binder and the tackifier, there can be mentioned, for example, carboxymethylcellulose or salt thereof, dextrin, water-soluble starch, xanthan gum, guar gum, sucrose, polyvinylpyrrolidone, gum arabic, polyvinyl alcohol, polyvinyl acetate, sodium polyacrylate, polyethylene glycol having an average molecular weight of 6,000 to 20,000, polyethylene oxide having an average molecular weight of 100,000 to 5,000,000, and phospholipid (e.g. cephalin or lecithin).

As the thickener, there can be mentioned, for example, water-soluble polymers such as xanthan gum, guar gum, carboxymethylcellulose, polyvinylpyrrolidone, carboxyvinyl polymer, acrylic polymer, starch derivative, polysaccharide and the like; and inorganic fine powders such as high-purity bentonite, fumed silica (fumed silica or white carbon) and the like.

As the coloring agent, there can be mentioned, for example, inorganic pigments such as iron oxide, titanium oxide, Prussian blue and the like; and organic dyes such as Alizarine dye, azo dye, metal phthalocyanine dye and the like.

As the spreader, there can be mentioned, for example, cellulose powder, dextrin, processed starch, polyaminocarboxylic acid chelate compound, crosslinked polyvinylpyrrolidone, maleic acid-styrene copolymer, (meth)acrylic acid copolymer, half ester between polymer (comprising polyhydric alcohol) and dicarboxylic acid anhydride, and water-soluble salt of polystyrene sulfonic acid.

As the sticker, there can be mentioned, for example, paraffin, terpene, polyamide resin, polyacrylic acid salt, polyoxyethylene, wax, polyvinylalkyl ether, alkylphenolformaldehyde condensate, and synthetic resin emulsion.

As the antifreezing agent, there can be mentioned, for example, polyhydric alcohols such as ethylene glycol, diethylene glycol, propylene glycol, glycerine and the like.

As the anticaking agent, there can be mentioned, for example, polysaccharides (e.g. starch, alginic acid, mannose and galactose), polyvinylpyrrolidone, fumed silica (fumed silica or white carbon), ester gum and petroleum resin.

As the collapsing agent, there can be mentioned, for example, sodium tripolyphosphate, sodium hexametaphosphate, metal stearate, cellulose powder, dextrin, methacrylic acid ester copolymer, polyvinylpyrrolidone, polyaminocarboxylic acid chelate compound, sulfonated styrene-isobutylene-maleic anhydride copolymer, and starch-polyacrylonitrile graft copolymer.

As the decomposition inhibitor, there can be mentioned, for example, desiccants such as zeolite, quick lime, magnesium oxide and the like; anti-oxidants such as phenol compound, amine compound, sulfur compound, phosphoric acid compound and the like; and ultraviolet absorbers such as salicylic acid compound, benzophenone compound and the like.

As the antiseptic agent, there can be mentioned, for example, potassium sorbate and 1,2-benzothiazolin-3-on.

As the piece of plant, there can be mentioned, for example, sawdust, coconut shell, corn rachis and tobacco stem.

When the above additive components are compounded in the agricultural or horticultural plant disease-controlling agent of the present invention, the proportions thereof is, on mass basis, ordinarily 5 to 95%, preferably 20 to 90% in the case of carrier; ordinarily 0.1% to 30%, preferably 0.5 to 10% in the case of surfactant; and 0.1 to 30%, preferably 0.5 to 10% in the case of other additives.

The agricultural or horticultural plant disease-controlling agent of the present invention is used by being prepared into various formulation forms such as liquid formulation, wettable powder, dust, oil solution, water dispersible granule, flowable, aqueous suspension concentrate, emulsifiable suspension concentrate, granule, Jumbo formulation, suspoemulsion and uniform diffusion formulation.

The agricultural or horticultural plant disease-controlling agent of the present invention, which contains the present invention compound (active ingredient), may be mixed as necessary, in various formulation forms mentioned above, with other known active compounds such as insecticide, acaricide, insect growth-controlling agent, nematicide, fungicide, plant disease-controlling agent, herbicide, plant growth-controlling agent, fertilizer, soil improver and the like.

Examples of the known fungicide compounds which may be mixed or used with the present plant disease-controlling agent, are shown below.

benomyl, carbendazim, fuberidazole, thiabendazole, thiophanate, thiophanate-methyl, chlozolinate, iprodione, procymidone, vinclozolin, azaconazole, bitertanol, bromuconazole, cyproconazole, difenoconazole, diniconazole, epoxiconazole, fenarimol, fenbuconazole, fluquinconazole, flusilazole, flutriafol, hexaconazole, imazalil, imibenconazole, ipconazole, metconazole, myclobutanil, nuarimol, oxpoconazole fumarate, paclobutrazol, pefurazoate, penconazole, prochloraz, propiconazole, prothioconazole, pyrifenox, simeconazole, tebuconazole, tetraconazole, triadimefon, triadimenol, triflumizole, triforine, triticonazole, benalaxyl, furalaxyl, metalaxyl, metalaxyl-M, ofurace, oxadixyl, aldimorph, dodemorph, fenpropidin, fenpropimorph, piperalin, spiroxamine, tridemorph, edifenphos, iprobenfos, isoprothiolane, pyrazophos, benodanil, boscalid, carboxin, fenfuram, flutolanil, furametpyr, mepronil, oxycarboxin, penthiopyrad, thifluzamide, bupirimate, dimethirimol, ethirimol, cyprodinil, mepanipyrim, pyrimethanil, diethofencarb, azoxystrobin, dimoxystrobin, enestrobin, famoxadone, fenamidone, fluoxastrobin, kresoximmethyl, metominostrobin, orysastrobin, picoxystrobin, pyraclostrobin, trifloxystrobin, fenpiclonil, fludioxonil, quinoxyfen, biphenyl, chloroneb, dicloran, etridiazole, quintozene, tecnazene, tolclofos-methyl, fthalide, pyroquilon, tricyclazole, carpropamid, diclocymet, fenoxanil, fenhexamid, pyributicarb, polyoxin, pencycuron, cyazofamid, zoxamide, blasticidin-S, kasugamycin, streptomycin, validamycin, cymoxanil, iodocarb, propamocarb, prothiocarb, binapacryl, dinocap, ferimzone, fluazinam, fentin acetate, fentin chloride, fentin hydroxide, oxolinic acid, hymexazol, octhilinone, fosetyl, phosphorus acid and salts (phosphonic acid), tecloftalam, triazoxide, flusulfamide, diclomezine, silthiofam, diflumetorim, benthiavalicarb-isopropyl, dimethomorph, flumorph, iprovalicarb, mandipropamid, oxytetracycline, methasulfocarb, chinomethionat, fluoroimide, milneb, copper hydroxide, copper octanoate, copper oxychloride, copper sulfate, cuprous oxide, mancopper, oxine-copper, sulfur, ferbam, mancozeb, maneb, metiram, propineb, thiram, zineb, ziram, captafol, captan, folpet, chlorothalonil, dichlofluanid, tolylfluanid, anilazine, dodine, guazatine, iminoctadine, dithianon, acibenzolar-S-methyl, probenazole, tiadinil, ethaboxam, cyflufenamid, proquinazid, metrafenone, fluopicolide, dazomet, difenzoquat, amisulbrom, Bordeaux mixture, tolnifanide, nabam, phenazine oxide, polycarbamate, pyribencarb Examples of the known insecticide and nematicide compounds which may be mixed or used in combination, are shown.

demeton-S-methyl, bioallethrin, famphur, DDT, DNOC, EPN, XMC, acrinathrin, azadirachtin, azamethiphos, azinphos-ethyl, azinphos-methyl, acequinocyl, acetamiprid, acetoprol, acephate, azocyclotin, abamectin, amitraz, alanycarb, aldicarb, alpha-cypermethrin, allethrin, isocarbophos, isoxathion, isofenphos, isoprocarb, imicyafos, imidacloprid, imiprothrin, indoxacarb, esfenvalerate, ethiofencarb, ethion, ethiprole, etoxazole, etofenprox, ethoprophos, emamectin, endosulfan, Empenthrin, oxamyl, oxydemeton-methyl, omethoate, cadusafos, cartap, carbaryl, carbosulfan, carbofuran, gamma-cyhalothrin, Lindane, xylylcarb, quinalphos, kinoprene, quinomethionate, coumaphos, clothianidin, clofentezine, chromafenozide, chlorethoxyfos, chlordane, chlorpyrifos, chlorpyrifos-methyl, chlorfenapyr, chlorfenvinphos, chlorfluazuron, chlormephos, cyenopyrafen, cyanophos, diafenthiuron, dienochlor, dicrotophos, dichlofenthion, cycloprothrin, dichlorvos, dicofol, disulfoton, dinotefuran, cyhalothrin, cyphenothrin, cyfluthrin, diflubenzuron, cyflumetofen, cyhexatin, cypermethrin, dimethylvinphos, dimethoate, tartar emetic, silafluofen, cyromazine, spinosad, spirodiclofen, spirotetramat, spiromesifen, sulfotep, zeta-cypermethrin, diazinon, tau-fluvalinate, thiacloprid, thiamethoxam, thiodicarb, thiocyclam, thiosultapsodium, thiofanox, thiometon, tetrachlorvinphos, tetradifon, tetramethrin, depallethrin, tebupirimfos, tebufenozide, tebufenpyrad, tefluthrin, teflubenzuron, temephos, deltamethrin, terbufos, tralomethrin, transfluthrin, triazamate, triazophos, trichlorfon, tribufos, triflumuron, trimethacarb, tolfenpyrad, naled, nicotine, nitenpyram, nemadectin, novaluron, noviflumuron, hydroprene, vamidothion, parathion, parathion-methyl, halfenprox, halofenozide, bioresmethrin, bistrifluron, pyridaphenthion, hydramethylnon, bifenazate, bifenthrin, piperonyl butoxide, pymetrozine, pyraclofos, pyridafenthion, pyridaben, pyridalyl, pyriproxyfen, pirimicarb, pyrimidifen, pirimiphos-methyl, pyrethrins, fipronil, fenazaquin, fenamiphos, fenisobromolate, fenitrothion, fenoxycarb, phenothrin, fenobucarb, fenthion, phenthoate, fentrifanil, fenvalerate, fenpyroximate, fenbutatin oxide, fenpropathrin, butocarboxim, butoxycarboxim, buprofezin, furathiocarb, pralethrin, fluacrypyrim, flucycloxuron, flucythrinate, flusulfamide, fluvalinate, flupyrazofos, fluvalinate, flupyrazofos, flufenerim, flufenoxuron, flubendiamide, flumethrin, flurimfen, prothiofos, flonicamid, propaphos, propargite, profenofos, propetamphos, propoxur, bromopropylate, beta-cyfluthrin, beta-cypermethrin, hexythiazox, hexaflumuron, heptenophos, permethrin, bensultap, benzoximate, bendiocarb, benfuracarb, borax, phoxim, phosalone, fosthiazate, phosphamidon, phosmet, formetanate, phorate, malathion, milbemectin, mecarbame, mesulfenfos, methomyl, metaflumizon, methamidophos, methamammonium, metham-sodium, methiocarb, methidathion, methoxychlor, methoxyfenozide, methothrin, methoprene, metolcarb, mevinphos, monocrotophos, lambda-cyhalothrin, rynaxypyr, aluminum phosphide, phosphine, lufenuron, resmethrin, lepmectin, rotenone, *Bacillus sphaericus, Bacillus thuringiensis* subsp. aizawai, *Bacillus thuringiensis* subsp. israelensis, *Bacillus thuringiensis* subsp. kurstaki, *Bacillus thuringiensis* subsp. tenebrionis, CL 900167 (test code), NNI-0101 (test code), RU 15525 (test code), XDE-175 (test code), ZXI 8901 (test code)

Examples of the known herbicide compounds which may be mixed or used in combination, are shown.

2,3,6-TBA, 2,4-D, 2,4-DB, DNOC, EPTC, HC-252 (test code), MCPA, MCPA-thioethyl, MCPB, S-metolachlor, TCA, ioxynil, aclonifen, azafenidin, acifluorfen, azimsulfuron, asulam, acetochlor, atrazine, anilofos, amicarbazone, amidosulfuron, amitrole, aminopyralid, amiprophos-methyl, ametryn, alachlor, alloxydim, ancymidol, iodosulfuron-methyl-sodium, isouron, isoxachlortole, isoxaflutole, isoxaben, isoproturon, imazaquin, imazapyr, imazamethabenz-methyl, imazapic, imazamox, imazethapyr, imazosulfuron, indanofan, esprocarb, ethametsulfuron-methyl, ethalfluralin, ethidimuron, ethoxysulfuron, ethofumesate, etobenzanid, oxadiazon, oxadiargyl, oxaziclomefone, oxasulfuron, oxyfluorfen, oryzalin, orbencarb, cafenstrole, carfentrazone-ethyl, karbutilate, carbetamide, quizalofop-P, quizalofop-P-ethyl, quizalofop-P-tefuryl, quizalofop-ethyl, quinclorac, quinmerac, cumyluron, glyphosate, glyphosate-trimesium, glufosinate, glufosinate-sodium, clethodim, clodinafop-propargyl, clopyralid, clomazone, chlomethoxyfen, clomeprop, cloransulam-methyl, chloramben, chloridazon, chlorimuron-ethyl, chlorsulfuron, chlorothal-dimethyl, chlorthiamid, chlorpropham, chlormequat chloride, chloroxuron, chlorotoluron, chlorobromuron, cyanazine, diuron, dicamba, cycloate, cycloxydim, diclosulam, cyclosulfamuron, dichlobenil, diclofop-methyl, dichlorprop, dichlorprop-P, diquat dibromide, dithiopyr, siduron, dinitramine, cinidon-ethyl, cinosulfuron, dinoseb, dinoterb, cyhalofop-butyl, di-phenamid, difenzoquat, diflufenican, diflufenzopyr, diflumetorim, simazine, dimethachlor, dimethametryn, dimethenamid, simetryn, dimepiperate, dimefuron, cinmethylin, sulcotrione, sulfentrazone, sulfosulfuron, sulfometuron-methyl, sethoxydim, terbacil, daimuron, dalapon, thiazopyr, tiocarbazil, thiobencarb, thidiazimin, thidiazuron, thifensulfuron-methyl, desmedipham, desmetryne, thenylchlor, tebutam, tebuthiuron, tepraloxydim, tefuryltrion, terbuthylazine, terbutryn, terbumeton, tembotrione, topramezone, tralkoxydim, triaziflam, triasulfuron, triallate, trietazine, triclopyr, triflusulfuronmethyl, tritosulfuron, trifluralin, trifloxysulfuronsodium, tribenuron-methyl, naptalam, naproanilide, napropamide, nicosulfuron, neburon, norflurazon, vernolate, paraquat dichloride, haloxyfop, haloxyfop-P, haloxyfop-P-methyl, halosulfuron-methyl, pinoxaden, picloram, picolinafen, bispyribac-sodium, bifenox, piperophos, pyraclonil, pyrasulfotole, pyrazoxyfen, pyrazosulfuron-ethyl, pyrazolynate, bilanafos, pyraflufen-ethyl, pyridafol, pyrithiobac-sodium, pyridate, pyriftalid, pyributicarb, pyribenzoxim, pyrimisulfan, primisulfuron-methyl, pyriminobac-methyl, pyroxysulam, fenuron, fenoxaprop-P-ethyl, fenoxapropethyl, fenclorim, fentrazamide, phenmedipham, foramsulfuron, butachlor, butafenacil, butamifos, butylate, butralin, butroxydim, flazasulfuron, flamprop-M, fluazifop-butyl, fluazifop-P-butyl, fluazolate, fluometuron, fluometuron, fluoroglycofen-ethyl, flucarbazone-sodium, flucetosulfuron, fluthiacet-methyl, flupyrsulfuron-methyl-sodium, flufenacet, flufenpyr-ethyl, flupropanate, flupoxame, flumioxazin, flumiclorac-pentyl, flumetsulam, fluridone, flurtamone, flurprimidol, fluroxypyr, fluorochloridone, pretilachlor, prodiamine, prosulfuron, prosulfocarb, propaquizafop, propachlor, propazine, propanil, propyzamide, propisochlor, propham, profluazol, propoxycarbazone, propoxycarbazone-sodium, profoxydim, bromacil, prometryn, prometon, bromoxynil, bromofenoxim, bromobutide, florasulam, hexazinone, pethoxamid, benazolin, penoxsulam, beflubutamid, pebulate, bencarbazone, pendimethalin, benzfendizone, bensulide, bensulfuron-methyl, benzobicyclon, benzofenap, bentazone, pentanochlor, pentoxazone, benfluralin, benfuresate, fosamine, fomesafen, forchlorfenuron, maleic hydrazide, mecoprop, mecoprop-P, mesosulfuron-methyl, mesotrione, metazachlor, methabenzthiazuron, metamitron, metamifop, methyldimuron, metoxuron, metosulam, metsulfuron-methyl, methobromuron, metobenzuron, metolachlor, metribuzin, mepiquat chloride, mefenacet, monolinuron, molinate, lactofen, linuron, rimsulfuron, lenacil, prohexadione-calcium, trinexapac-ethyl Processes for producing the present invention compound represented by the general formula [I], methods for producing the agricultural or horticultural plant disease-controlling agent of the present invention, and applications of the plant disease-controlling agent are described specifically below in the following Examples. However, the present invention is in no way restricted to these Examples. Incidentally, in the following description, % is percent by weight.

Example 1

Production of (3,4-dichloroisothiazol-5-yl)methyl benzoate (Present Invention Compound No. II-1)

To 4.0 g (20.3 mmol) of 3,4-dichloroisothiazole-5-carboxylic acid were added 8 ml of oxalyl chloride and a catalytic amount of N,N-dimethylformamide (DMF). The mixture was stirred at 50° C. for 30 minutes. The reaction mixture was concentrated under vacuum to obtain 3,4-dichloroisothiazole-5-carbonyl chloride.

1.9 g (50.5 mmol) of sodium borohydride was suspended in 40 ml of water. To the suspension was dropwise added, at 10 to 15° C., a THF (4 ml) solution of the above-produced 3,4-dichloroisothiazole-5-carbonyl chloride. The mixture was stirred at 15° C. for 30 minutes. Then, an aqueous citric acid solution was added to the mixture to make it weakly acidic, followed by extraction with ethyl acetate. The organic layer was washed with water, dried over anhydrous magnesium sulfate, and concentrated. The resulting crystals were washed with hexane to obtain 3.0 g (yield: 81%) of (3,4-dichloroisothiazol-5-yl)methanol as colorless crystals (melting point: 94 to 95° C.).

$^1$H-NMR data (CDCl$_3$/TMS δ (ppm))

2.28 (1H, bs), 4.96 (2H, s) ppm 3.0 g (16.3 mmol) of the above-produced (3,4-dichloroisothiazol-5-yl)methanol and 2.52 g (17.9 mmol) of benzoyl chloride were dissolved in 70 ml of toluene. Thereto was dropwise added, under ice-cooling, 1.98 g (19.6 mmol) of triethylamine. The mixture was stirred at room temperature for 3 hours. Water was added, followed by extraction with ethyl acetate. The organic layer was washed with water, dried over anhydrous magnesium sulfate, and concentrated. The resulting crystals were washed with hexane to obtain 4.1 g (yield: 87%) of (3,4-dichloroisothiazol-5-yl)methyl benzoate as colorless crystals (melting point: 79 to 80° C.).

$^1$H-NMR data (CDCl$_3$/TMS δ (ppm)):

5.54 (2H, s), 7.45-7.50 (2H, m), 7.59-7.64 (1H, m), 8.05-8.08 (2H, m)

Example 2

Production of (3,4-dichloroisothiazol-5-yl)methyl thioacetate (Present Invention Compound No. I-28)

To a THF (50 ml) solution of 2.85 g (10.9 mmol) of triphenylphosphine was added, under ice-cooling, 2.2 g (10.9 mmol) of diisopropyl azodicarboxylate, followed by stirring for 30 minutes. To the solution was added a THF (5 ml) solution of 1.0 g (5.43 mmol) of (3,4-dichloroisothiazol-5-yl)methanol and 0.83 g (10.9 mmol) of thioacetic acid, followed by stirring at room temperature for 5 hours, to give rise to a reaction. After the completion of the reaction, ethyl acetate was added to the reaction mixture. The resulting mixture was washed with water, dried over anhydrous magnesium sulfate and concentrated. The residue was purified by silica gel column chromatography to obtain 0.42 g (yield: 32%) of (3,4-dichloroisothiazol-5-yl)methyl thioacetate as a light red oily substance (refractive index: 1.5855).

$^1$H-NMR data (CDCl$_3$/TMS δ (ppm)):

2.41 (3H, s), 4.24 (2H, s)

The properties of the present invention compounds [I] produced in the above Examples and the present invention compounds [I] produced based on the above Examples are shown in Table 11. Incidentally, compound Nos. are referred to in the later description.

TABLE 11

| Compound No. | Melting point (° C.) or Refractive index ($n^D_{20}$) | |
|---|---|---|
| I-1 | Refractive index | 1.5393 |
| I-24 | Melting point | 70-72 |
| I-28 | Refractive index | 1.5855 |
| II-1 | Melting point | 79-80 |
| II-5 | Melting point | 60-61 |
| II-14 | Melting point | 50-53 |
| II-17 | Melting point | 107-108 |
| II-24 | Refractive index | 1.5714 |
| II-55 | Melting index | 101-102 |
| II-57 | Melting index | 66-67 |
| II-66 | Melting index | 100-101 |
| II-77 | Melting index | 66-69 |
| II-78 | Melting index | 92-94 |
| II-79 | Melting index | 100-102 |
| II-82 | Melting index | 106-107 |
| III-1 | Melting index | 92-93 |

TABLE 11-continued

| Compound No. | Melting point (° C.) or Refractive index ($n^D_{20}$) | |
|---|---|---|
| III-9 | Melting index | 131-132 |
| III-29 | Melting index | 147-148 |

For compound Nos. I-1 and II-14, their $^1$H-NMR data (CDCl$_3$/TMS δ (ppm)) are shown below.

Compound No. I-1: 2.15 (3H, s), 5.29 (2H, s)

Compound No. II-14: 3.87 (3H, s), 5.53 (2H, s), 7.57-7.61 (2H, m), 7.70-7.73 (1H, m), 7.77-7.81 (1H, m)

Next, the method for preparation of the present controlling agent is specifically described on representative controlling agents. The kinds of compounds and additives used, and the compounding ratios thereof are not restricted to those shown below and can be varied in wide ranges. In the following description, "parts" refer to parts by weight.

Example 3

Dust

| | |
|---|---|
| Compound No. I-1 | 2 parts |
| Diatomaceous earth | 5 parts |
| Clay | 93 parts |

The above substances were uniformly mixed and ground to obtain a dust. The compound No. I-1 was replaced by other compounds shown in Table 1 to Table 10, whereby dusts could be obtained in the same manner.

Example 4

Wettable Powder

| | |
|---|---|
| Compound No. II-1 | 50 parts |
| Diatomaceous earth | 45 parts |
| Sodium dinaphthylmethanedisulfonate | 2 parts |
| Sodium ligninsulfonate | 3 parts |

The above substances were uniformly mixed and ground to obtain a wettable powder. The compound No. II-1 was replaced by other compounds shown in Table 1 to Table 10, whereby wettable powders could be obtained in the same manner.

Example 5

Wettable Powder

| | |
|---|---|
| Compound No. 11-17 | 10 parts |
| Clay | 69 parts |
| Diatomaceous earth | 20 parts |
| Sodium salt of β-naphthalenesulfonic acid formalin Condensate | 0.5 part |
| Polyoxyethylene octyl phenyl ether | 0.5 part |

The above substances were uniformly mixed and ground to obtain a wettable powder. The compound No. II-17 was replaced by other compounds shown in Table 1 to Table 10, whereby wettable powders could be obtained in the same manner.

Example 6

Emulsifiable Concentrate

| | |
|---|---|
| Compound No. I-1 | 30 parts |
| Cyclohexanone | 20 parts |
| Polyoxyethylene alkyl aryl ether | 11 parts |
| Calcium alkylbenzenesulfonate | 4 parts |
| Methylnaphthalene | 35 parts |

The above substances were uniformly dissolved to obtain an emulsifiable concentrate. The compound No. I-1 was replaced by other compounds shown in Table 1 to Table 10, whereby emulsifiable concentrates could be obtained in the same manner.

Example 7

Granule

| | |
|---|---|
| Compound No. II-1 | 4 parts |
| Sodium salt of lauryl alcohol sulfate | 2 parts |
| Sodium ligninsulfonate | 5 parts |
| Carboxymethyl cellulose | 2 parts |
| Clay | 87 parts |

The above substances were uniformly mixed and ground. Thereto was added 20 parts of water, followed by kneading. The kneaded product was processed into a granular material of 14 to 32 meshes using an extruding granulator, followed by drying, to obtain granule. The compound No. II-1 was replaced by other compounds shown in Table 1 to Table 10, whereby granules could be obtained in the same manner.

Next, the effect shown by the agricultural or horticultural plant disease-controlling agent of the present invention is specifically described by way of Test Examples.

Test Example 1

Test for Prevention of Rice Blast Disease in Submerged Application

Paddy rice plant of 2.5- to 3-leaf stage (variety: Aichi Asahi) was transplanted into a white porcelain basin of 9 cm in diameter (each three paddy rice plants were transplanted at 4 different places) and was grown in a greenhouse. A wettable powder prepared in accordance with Example 5 was diluted with water and 5 ml of the resulting chemical solution was applied so that the amount of active ingredient became 10 g per 10 ares. The paddy rice plant treated with the chemical solution was grown in the greenhouse. 10 days after the treatment, the grown paddy rice plant was inoculated with a conidia suspension ($10^5$/ml) of Pyricularia oryzae by spraying in a moist chamber of 25° C., and infection was allowed to take place for 24 hours. Then, the paddy rice plant was transferred into the greenhouse and, 6 days after the inoculation, the number of lesions on the fully developed leaf which had been latest at the inoculation, was examined. A protective value was calculated from the following mathematical expression 1 and evaluated according to the standard of Table 12. The result is shown in Table 13.

Protective value=[1−(the number of lesions in treated plants)/(the number of lesions in untreated plants)]×100  [Expression 1]

TABLE 12

| Evaluation |
| --- |
| A: protective value: 100% to 90.0% or more |
| B: protective value: less than 90.0% to 80.0% or more |
| C: protective value: less than 80.0% to 50.0% or more |
| D: protective value: less than 50.0% |

Using a comparative compound shown below, a wettable powder was prepared according to Example 5. A protective value thereof was calculated in the same manner as in the above Test Example. The result is shown in Table 13.

[Formula 5]

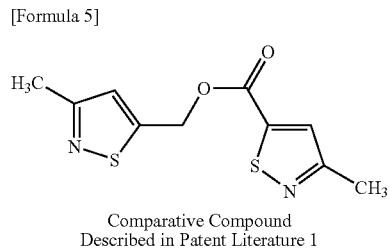

Comparative Compound
Described in Patent Literature 1

TABLE 13

| Compound No. | Applied amount of active ingredient (g a.i./10 a) | Evaluation | Protective value |
| --- | --- | --- | --- |
| I-1 | 10 | A | 96.1 |
| I-24 | 10 | A | 95.2 |
| I-28 | 10 | C | 79.9 |
| II-1 | 10 | A | 92.3 |
| II-5 | 10 | A | 94.6 |
| II-14 | 10 | A | 92.4 |
| II-17 | 10 | A | 98.2 |
| II-24 | 10 | A | 98.3 |
| II-55 | 10 | A | 98.8 |
| II-57 | 10 | A | 98.4 |
| II-66 | 10 | A | 97.8 |
| II-77 | 10 | C | 74.1 |
| II-78 | 10 | C | 77.5 |
| II-79 | 10 | A | 92.3 |
| II-82 | 10 | B | 88.0 |
| III-1 | 10 | B | 81.3 |
| III-9 | 10 | B | 85.9 |
| III-29 | 10 | A | 90.5 |
| Comparative compound | 10 | D | 45.9 |

Test Example 2

Test for Preventive Effect for Cucumber Anthracnose

Four cucumber seeds (variety: Sagamihanjiro) were sowed in a plastic cup of 5.5 cm in diameter, at a depth of 2 cm, and were grown in a greenhouse for 7 days. One of wettable powders prepared according to Example 5 was diluted with water so that the concentration of active ingredient became a given level. 10 ml of the dilution was poured into the soil at the root of young cucumber seedlings having cotyledons. 7 days later, a conidia suspension ($10^5$ to $10^6$/ml) of Colletotrichum orbiculare which had been cultured in a PDA plate medium, was uniformly inoculated to the cucumber plant by hand spraying. The cup was allowed to stand, for infection, in a moist chamber of 25° C. for 24 hours. Then, the cup was allowed to stand on a basin in a glass greenhouse and, 7 day later, the number of lesions of all cotyledons in pot was examined. A protective value was calculated from the above expression 1 and evaluated according to the standard of Table 12. The result is shown in Table 14.

Using the above-shown comparative compound, a wettable powder was prepared according to Example 5. A protective value thereof was calculated in the same manner as in the above Test Example. The result is shown in Table 14.

TABLE 14

| Compound No. | Applied amount of active ingredient (ppm) | Evaluation | Protective value |
| --- | --- | --- | --- |
| I-1 | 1 | B | 86.9 |
| I-24 | 1 | B | 89.1 |
| II-1 | 1 | B | 89.1 |
| III-1 | 1 | A | 98.4 |
| III-9 | 1 | A | 94.0 |
| III-29 | 1 | A | 94.5 |
| Comparative compound | 1 | C | 73.3 |

Test Example 3

Test for Preventive Effect on Powdery Mildew of Wheat 10 wheat seeds (variety: Nohrin No. 61) were sowed in a plastic cup of 5.5 cm in diameter and were grown in a greenhouse for 7 days. One of wettable powders prepared in accordance with Example 5 was diluted with water so that the concentration of active ingredient became 500 ppm, a spreader (brand name: KUMITEN) was added for the dilution factor to be 3,000 times, and a sufficient amount of the resulting solution was sprayed onto the wheat of 1.5- to 2-leaf stage. After air-drying, a conidia suspension of Erysiphe graminis was sprayed for inoculation. The wheat leaves were allowed to stand in the greenhouse until a development of disease. 7 days later, the disease development indices of the first leaves of the pot were examined according to the standard of Table 15. The disease development degrees were calculated from the following expression 2. A protective value (%) was calculated from the following expression 3.

TABLE 15

| Disease development index |
| --- |
| 0: No disease outbreak |
| 1: Disease developed area: less than 25% |
| 2: Disease developed area: 25% to less than 50% |
| 3: Disease developed area: 50% to less than 75% |
| 4: Disease developed area: 75% or more |

Disease development degree=$[(n0×0+n1×1+n2×2+n3×3+n4×4)/4×N]×100$  [Expression 2]

In the above expression 2,
N: number of total leaves examined
n0: number of leaves of disease development degree 0
n1: number of leaves of disease development degree 1 n2: number of leaves of disease development degree 2
n3: number of leaves of disease development degree 3
n4: number of leaves of disease development degree 4

Protective value=[1−(disease development degree in treated plants)/(disease development degree in untreated plants)]×100  [Expression 3]

Representative of those compounds which showed a protective value of 75% or more in the above test, are compounds Nos. I-24, II-1, II-5, II-24, II-55, II-57, II-79, II-82, etc.

Test Example 4

Test for Preventive Effect for Rice Blast Disease

One of wettable powders prepared in accordance with Example 5 was diluted with water so that the concentration of active ingredient became 500 ppm, a spreader (brand name: KUMITEN) was added for the dilution factor to be 3,000 times, and a sufficient amount of the resulting solution was uniformly sprayed, using a spray gun, onto the 10 paddy rice plant (variety: Aichi Asahi) seedlings of 4-leaf stage which had been grown in an unglazed pot of 7.5 cm in diameter. After air-drying, the seedlings were inoculated, by spraying, with a conidia suspension ($10^5$/ml) of Pyricularia oryzae, in a moist chamber of 25° C., and infection was allowed take place for 24 hours. Then, the seedlings were transferred into a greenhouse. 5 days after the inoculation, the number of lesions of each fourth-leaf was examined. A protective value was calculated from the above-shown expression 1.

Representative of those compounds which showed a protective value of 80% or more in the above test, are compounds Nos. II-17, II-24, etc.

Test Example 5

Test for Preventive Effect on Wheat Glume Blotch 10 wheat seeds (variety: Nohrin No. 61) were sowed in a plastic cup of 5.5 cm in diameter and were grown in a greenhouse for 7 days. One of wettable powders prepared in accordance with Example 5 was diluted with water so that the concentration of active ingredient became 500 ppm, a spreader (brand name: KUMITEN) was added for the dilution factor to be 3,000 times, and a sufficient amount of the resulting solution was sprayed onto the leaves of wheat (1.5- to 2-leaf stage) using a spray gun. After air-drying, a suspension of the pycniospores of Stagonospora nodorum was sprayed for inoculation. Immediately thereafter, the wheat leaves were transferred into a moist chamber of 25° C. and allowed to stand under a bright condition for 48 hours for infection. Then, the wheat leaves were transferred into the greenhouse and, 12 days after the inoculation, the disease development index of each first leaf was examined according to the standard of Table 15. A disease development degree was calculated from the above expression 2. A protective value (%) was calculated from the above expression 3 and evaluated according to the standard of Table 16. The result is shown in Table 17.

TABLE 16

| Evaluation |
| --- |
| A: protective value: 100% to 75% or more |
| B: protective value: less than 75% to 50% or more |

TABLE 16-continued

| Evaluation |
| --- |
| C: protective value: less than 50% to 25% or more |
| D: protective value: less than 25% |

TABLE 17

| Compound No. | Applied amount of active ingredient (ppm) | Evaluation |
| --- | --- | --- |
| II-5 | 500 | A |
| II-14 | 500 | B |
| II-24 | 500 | A |
| II-55 | 500 | A |
| II-57 | 500 | A |
| II-66 | 500 | A |
| II-77 | 500 | A |
| II-78 | 500 | B |
| II-79 | 500 | A |
| II-82 | 500 | A |
| III-1 | 500 | B |
| Comparative compound | 500 | D |

The invention claimed is:

1. A 3,4-dihalogenoisothiazole derivative represented by the general formula [I]

[formula 1]

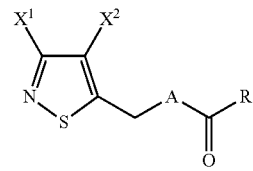

[wherein $X^1$ and $X^2$ are each a halogen atom;
A is an oxygen atom or a sulfur atom; and
R is a phenyl group (the group may be mono- or poly-substituted by same or different substituents selected from the following substituents group α), or a 5- to 10-membered heterocyclic group containing at least one of oxygen atom, sulfur atom and nitrogen atom (the group may be mono- or poly-substituted by same or different substituents selected from group α, or a salt thereof; wherein group a consists of:
$C_1$-$C_6$ alkyl group, $C_3$-$C_6$ cycloalkyl group, $C_1$-$C_6$ haloalkyl group, phenyl group, halogen atom, cyano group, $C_1$-$C_6$ acyl group, carboxyl group, $C_1$-$C_6$ alkoxycarbonyl group, mono($C_1$-$C_6$ alkyl)carbamoyl group, di($C_1$-$C_6$ alkyl)carbamoyl group, amino group, mono ($C_1$-$C_6$ alkyl)amino group, di($C_1$-$C_6$ alkyl)amino group, $C_1$-$C_6$ alkylamide group, $C_1$-$C_6$ alkylsulfonamide group, nitro group, hydroxyl group, $C_1$-$C_6$ alkoxy group, $C_1$-$C_6$ acyloxy group, $C_1$-$C_6$ alkylsulfonyl group, mono ($C_1$-$C_6$ alkyl)sulfamoyl group, and di($C_1$-$C_6$ alkyl)sulfamoyl group.

2. A 3,4-dihalogenoisothiazole derivative or a salt thereof, according to claim 1, wherein R is a 5- to 10-membered heterocyclic group selected from the group consisting of pyrrole, furan, thiophene, oxazole, thiazole, imidazole, isoxazole, isothiazole, pyrazole, oxadiazole, thiadiazole, triazole, indole, benzofuran, benzothiophene, benzoxazole, benzothiazole, benzoimidazole, benzoisoxazole, benzoisothiazole, indazole, benzoxadiazole, benzothiadiazole, and benzotriazole, wherein the heterocyclic group is optionally mono- or poly-substituted by the same or different substituents selected from group α.

3. A 3,4-dihalogenoisothiazole derivative or a salt thereof, according to claim 1, wherein R is a phenyl group (the group may be substituted by same or different, 1 to 5 substituents selected from the group consisting of $C_1$-$C_6$ alkyl group, halogen atom, cyano group, $C_1$-$C_6$ alkoxycarbonyl group, nitro group, $C_1$-$C_6$ alkoxy group and $C_1$-$C_6$ alkylsulfonyl group), pyridine (the group may be substituted by same or different, 1 to 4 substituents selected from the group consisting of $C_1$-$C_6$ alkyl group and halogen atom), isothiazole (the group may be substituted by same or different, 1 to 2 substituents selected from the group consisting of $C_1$-$C_6$ alkyl group and halogen atom), or benzothiadiazole (the group may be substituted by same or different, 1 to 3 substituents selected from the group consisting of $C_1$-$C_6$ alkyl group and halogen atom).

4. An agricultural or horticultural plant disease-controlling agent containing, as an active ingredient, a 3,4-dihalogenoisothiazole derivative or a salt thereof, according to claim 1.

5. A 3,4-dihalogenoisothiazole derivative or a salt thereof, according to claim 1, wherein R is a phenyl group (the group may be substituted by same or different, 1 to 5 substituents selected from the group consisting of $C_1$-$C_6$ alkyl group, halogen atom, cyano group, $C_1$-$C_6$ alkoxycarbonyl group, nitro group, $C_1$-$C_6$ alkoxy group and $C_1$-$C_6$ alkylsulfonyl group), pyridine (the group may be substituted by same or different, 1 to 4 substituents selected from the group consisting of $C_1$-$C_6$ alkyl group and halogen atom, isothiazole (the group may be substituted by same or different, 1 to 2 substituents selected from the group consisting of $C_1$-$C_6$ alkyl group and halogen atom), and benzothiadiazole (the group may be substituted by same or different, 1 to 3 substituents selected from the group consisting of $C_1$-$C_6$ alkyl group and halogen atom).

6. An agricultural or horticultural plant disease-controlling agent containing, as an active ingredient, a 3,4-dihalogenoisothiazole derivative or a salt thereof, according to claim 5.

* * * * *

UNITED STATES PATENT AND TRADEMARK OFFICE
CERTIFICATE OF CORRECTION

PATENT NO. : 8,003,675 B2
APPLICATION NO. : 12/227397
DATED : August 23, 2011
INVENTOR(S) : Toshihiro Nagata et al.

It is certified that error appears in the above-identified patent and that said Letters Patent is hereby corrected as shown below:

Col. 30, line 50, "a" should read --$\alpha$--.

Col. 30, line 53, "$C_1 - C_6$ acyl" should read --$C_1 - C_5$ acyl--.

Signed and Sealed this
Twenty-fifth Day of October, 2011

David J. Kappos
*Director of the United States Patent and Trademark Office*